United States Patent [19]

Hughes et al.

[11] Patent Number: 4,876,355

[45] Date of Patent: Oct. 24, 1989

[54] POWDERED IMIDAZOLINE PRODUCT AND METHOD FOR PRODUCING SAME

[75] Inventors: Leonard Hughes; James G. Fuller, both of Dublin; Gary W. Earl, Bexley, all of Ohio

[73] Assignee: Sherex Chemical Company, Inc., Dublin, Ohio

[21] Appl. No.: 278,200

[22] Filed: Oct. 21, 1988

[51] Int. Cl.$^4$ ............................................. C07D 233/18
[52] U.S. Cl. ..................................................... 548/352
[58] Field of Search ......................................... 548/352

[56] References Cited

U.S. PATENT DOCUMENTS 4,233,451 11/1980 Pracht et al. ................... 548/352 X
4,269,730 5/1981 Wechsler et al. .................... 252/356
4,709,045 11/1987 Kubo et al. ........................... 548/352

Primary Examiner—Richard A. Schwartz
Attorney, Agent, or Firm—Mueller and Smith

[57] ABSTRACT

Disclosed is a stable, free-flowing particulate imidazoline product of the structure:

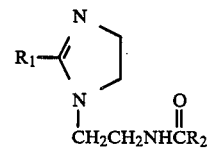

where $R_1$ and $R_2$ independently are a saturated $C_{12}$–$C_{22}$ alkyl group. The product is made by condensing and cyclyzing a fatty acid or ester and a polyamine wherein the molten, cyclyzed, solvent-free product is rapidly cooled to a particulate form.

10 Claims, No Drawings

POWDERED IMIDAZOLINE PRODUCT AND METHOD FOR PRODUCING SAME

BACKGROUND OF THE INVENTION

Imidazolines are a family of compounds based on a five-membered ring structure containing two nitrogen atoms and a double bond. The ring is numbered in such fashion that the nitrogens carry the lowest combinations of numbers:

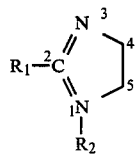
(I)

Commercially, imidazolines are made from the reaction of fatty acid, fatty alkyl (e.g. methyl) esters, or fatty triglycerides with a polyamine such as, diethylenetriamine (DETA), aminoethylethanolamine (AEEA), ethylenediamine (EDA), or triethylenetetramine (TETA). The intermediate amidoamine is dehydrated to yield the cyclic imidazoline product.

While the manufacture of imidazolines on a commercial scale is relatively easy, the product is not easy to store or use without hydrolysis. Numerous authors have commented on the instability of the imidazoline molecule. Linfield, *JAOCS*, 61, No. 2 (1984), p 439, states that the imidazolines are unstable and in the presence of water revert to the amidoamine starting material by standing overnight at room temperature. Wechsler, et al., U.S. Pat. Nos. 4,269,730 and 4,189,593, caution that during the reduced pressure dehydration to make the imidazoline, care must be taken to avoid any contact between the reactant and air which would cause rapid and severe darkening of the product. Butler, et al., *J. Chem. Res.*, (5), 84 (1981) report decomposition of the imidazoline ring under atmospheric conditions in 2-9 days provided the compound contains a cis-olefin system. Bristline, et al., *JAOCS*, 60, No. 4 (1983), p 823, showed that the imidazoline ring content in a system decreased from 38% to 6% imidazoline in 72 hours with the addition of 2% $H_2O$ (half-life of 24 hours). Even in a sealed container, these authors reported 5-8% loss in ring content over 18 months. Their conclusion was that, "When used as intermediates, imidazolines should be reacted promptly and prolonged storage should be avoided". Bristline, et al., *JAOCS*, 60, (1983), p 1676, showed that, "The imidazoline is hydrolyzed quantitatively to the diamide in the presence of water in ca. four days at room temperature."

This well-documented hydrolytic instability has inhibited the commercialization of imidazolines for aqueous applications. When imidazolines are protonated or quaternized, however, their hydrolytic stability is dramatically increased as is their water compatibility. Commercial producers, then, often manufacture the protonated or quaternized derivatives of imidazolines. Imidazolone-derived amphoterics are known to be excellent foamers and good cleaners, yet are substances of low toxicity possessing properties of low-irritancy to both skin and eye. Hunting, "Amphoteric Surfactants", *Cosmetics & Toiletries*, 95, November, 1980, p 95, and references cited therein, reports that these amphoterics also are bacteriostatic.

Certain fatty imidazoline derivatives are liquid material at ambient temperature. These materials are derived from highly unsaturated fatty acid sources such as, for example, tall oil, soya oil, and oleic acid. These types of imidazolines usually are used in applications where light color is not required as they tend toward darker colors due to the characteristics of the sources for unsaturated fatty acids and oils. Hydrogenated fatty acids and esters typically yield light colored products, but also produce higher melting point materials when converted to imidazolines.

Despite the foregoing, commonly-assigned application U.S. Ser. No. 07/155,768, filed Feb. 16, 1988, discloses an imidazoline product which is light-colored and color-stabilized. Such product is formed by pretreating the polyamine reactant with an effective amount of a hydride prior to the amide-forming reaction with a fatty acid or ester. The resulting stabilized imidazoline product is reported to be storable as a liquid under conventional liquid imidazoline-storage conditions for a sufficient time to permit the product to be shipped from the manufacturing site to another location whereat the imidazoline product is to be used. This time period is reported to range from a few days to two weeks or so. Despite this significant advance in the handling and storage of liquid imidazolines, further extension of shelf life is desirable.

BROAD STATEMENT OF THE INVENTION

The present invention is directed to an imidazoline product which can be stored in ordinary containers for several months and remain quite stable for use. Broadly, the present invention comprises a stable, free-flowing particulate imidazoline product of the structure

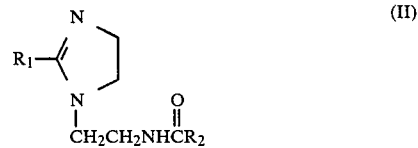
(II)

where $R_1$ and $R_2$ independently are a saturated $C_{12}$–$C_{22}$ alkyl group. The imidazoline product is made by condensing and cyclizing a fatty acid or ester and a polyamine, wherein the molten, cyclized, solvent-free product is rapidly cooled to particulate form. The preferred rapid cooling process comprises prilling or spray cooling utilizing a prilling or cooling tower and a spinning disk, for example. No special precautions with respect to humidity control or oxygen control need be provided during this atomization operation. The method of forming the stable, free-flowing particulate imidazoline product forms yet another aspect of the present invention.

Advantages of the present invention include the ability to provide an imidazoline product in a convenient form which is easy to store and use. Another advantage is an imidazoline product which is remarkably stable in the presence of atmospheric moisture and atmospheric oxygen. Yet another advantage is an imidazoline product which can be converted into a stable, easily-handleable form without taking special precautions during the particulate-forming operation. These and other advantages will be easily apparent to those skilled in the art based upon the disclosure contained herein.

DETAILED DESCRIPTION OF THE INVENTION

Imidazolines are manufactured, stored, and transported in the substantial absence of oxygen for minimizing color degradation of the product. Good quality nitrogen can contain up to 2% oxygen while liquid nitrogen normally contains about 10 ppm oxygen or thereabouts. Even using liquid nitrogen as the source for the gas blanket which fills the headspace in the container, the imidazoline liquid product will lose color over time. Thus, little commercial use of imidazolines have been made where a light colored product is necessary. It is not unusual for the manufacturing and the use sites to be located quite a distance apart, thus necessitating transportation and storage times of a few days to a few weeks being required of the imidazoline product. By providing a particulate imidazoline product not prone to color degradation, the formulator will be presented a lighter colored product, thus enabling the formulator to dye the final formulation to a pleasing appearance. Moroever, the imidazoline product can be converted into a variety of final forms including, for example, an amine salt in situ when dispersed in acid aqueous solutions in the formulation of fabric softener dispersions. The imidazoline product, not being a quaternary ammonium compound, can be added to anionic compounds without fear of complexing, thus offering the opportunity to develope unique detergency/softening/anti-static properties not obtained when quaternary ammonium compounds are used, for example, in laundry products where anionic/cationic complexes can form.

Unexpectedly, it was discovered that when the molten, cyclized, solvent-free imidazoline product was rapidly cooled and provided in particulate form, that it could be stored and handled without the necessity of extraordinary precaution precluding admission of atmospheric oxygen and/or atmospheric moisture, yet maintain its free-flowing particulate nature without apparent loss of imidazoline content which would render the product unsuitable for its intended uses. Even the particulate-forming operation, such as a spray chilling operation, can be conducted under ordinary conditions wherein prevailing environmental air can be used in the tower wherein the particulates are formed. The product has been stored in 2,000 pound sacks with samples taken from the bottom over a six month period. These samples revealed that the product retained its free-flowing nature with virtually no imidazoline content lost. Truly, such results are remarkable.

The reasons for such stability of the product are not fully understood presently. A variety of theories can be postulated as to why the oxygen and moisture sensitive imidazoline product as reported in the literature appears to be substantially unaffected by oxygen and water when produced and provided in the novel form disclosed herein. Since none of these theories have been fully evaluated, they will not be speculated upon herein. It is important only that the stable, free-flowing nature of the imidazoline particulate product can be produced economically and reliably at commercial scale operations to produce a product possessing the characteristics disclosed herein.

The first step in forming the novel particulate imidazoline product of the present invention comprises the reaction of a fatty acid or fatty acid ester reactant with a polyamine under amide-forming reaction conditions.

The polyamine can be hydride pretreated in accordance with U.S. Ser. No. 07/155,768, discussed above, or the resulting imidazoline liquid product can be hydride treated as disclosed in U.S. Pat. No. 3,468,904. Regardless of whether the hydride stabilization step is practiced, the fatty acid or ester reactant and polyamine are reacted under amide-forming conditions which comprehend the temperature in excess of 100° C. and usually in the range of about 125° to 300° C. for reaction times ranging from about 4 to 12 hours. After the amide intermediate has formed, application vacuum with resultant water distillation from the reaction mixture results in the formation of the cyclic imidazoline product.

It appears important in the formation of the stable particulate imidazoline product that the fluent cyclic imidazoline product as-made is not cooled, but is maintained in its liquid, fluent state at elevated temperature and admitted directly into a particulate-forming operation. That is, since the imidazoline product is solid at room temperature, the as-made molten imidazoline product should not be cooled to solidification and reheated for forming the particulates of the present invention unless loss of imidazolline content can be tolerated. Also, the imidazoline product should not be dispersed in solvent for maintaining its fluidity for admission to a particulate forming operation.

A wide variety of techniques are known in the art for converting molten, fluent material to particulate form. The use of spray chilling involving spray nozzles, spinning disks, spinning bells, and like techniques are well known in the art. The particle size range desirably is between about 50 and 150 microns in average particle size. Alternatively, the molten, fluent imidazoline product can be admitted onto chilled rolls for rapidly forming solid sheets of the imidazoline product which then are subjected to an attrition operation for forming imidazoline particulates. Of course, the type and degree of milling will determine the final particle size of the imidazoline product. Other techniques may be envisioned for rapidly solidifying the molten imidazoline for rapidly forming particulates thereof. As noted above, during these operations, normal handling techniques for the equipment used can be maintained. That is, as the Examples will demonstrate with respect to use of a chilling tower and spinning disk, the prevailing atmospheric conditions, including relative humidity, in the plant were not altered in the spray chilling operation. The lack of need for special handling techniques contributes to the overall economies and efficiencies of the process.

With respect to imidazolines, the literature is replete in descriptions of suitable polyamines and suitable fatty acids or esters thereof useful in imidazoline formation. Briefly, fatty acids typically are monobasic aliphatic acids containing from about 8 to 30 carbon atoms and more often from about 12 to 22 carbon atoms. Typically, fatty acids are derived from natural triglyceride sources, e.g. vegetable oils, though they may be derived from animal, fish, or nut oil, or they may be synthetic in nature. Esters of such fatty acids also can be used as is well known in the art.

Briefly, polyamines useful in making imidazolines include ethylene diamine, diethylene, triamine, triethylene tetramine, aminoethylethanol amine, hydroxyethyl diethylene triamine, and the like and mixtures thereof. The foregoing list of fatty acids and polyamines merely is exemplary of the broad nature of imidazolines which can be stabilized in accordance with the precepts of the present invention. Anti-oxidants and/or sequestrants can be used in the stabilized imidazoline liquid product as is necessary, desirable, or convenient in conventional fashion. Preferred imidazolines for use in the invention include, for example, 1-[hydrogenated tallow amido ethyl],2-hydrogenated tallow imidazoline (also the fractionated tallow imidazoline) and 1-[coco amido ethyl],2-coco imidazoline.

The following example shows how the present invention has been practiced but should not be construed as limiting. In this application, all percentages and proportions are by weight unless otherwise expressly indicated. Also, all citations disclosed herein are expressly incorporated herein by reference.

EXAMPLE

1-[hydrogenated tallow amido ethyl],2-hydrogenated tallow imidazoline made at a commercial plant operating in this country was spray congealed in an industrial spray tower. The imidazoline feedstock had a color of 3 expressed in Gardner units. The feedstock was fed to the spray chiller at the rate of about 70 pounds per minute. The temperature/humidity in the spray chiller was the ambient air prevailing at the plant. Test runs were conducted during various seasonal time periods, including July, with no special provision being made for dehumidifying the air in the chiller nor utilizing a nitrogen atmosphere.

The powdered imidazoline product obtained from the spray chiller had a particle size of about 100 microns and was in free-flowing particulate form. A test melt of the product indicated a Gardner color of 4, a loss of only one unit from the feedstock. This material was stored in 2,000 pound sacks with samples taken from the bottom over a six month period. These samples revealed that the product retained its free-flowing nature.

Using U.V. spectroscopy, the feedstock was shown to have a ring content of about 96%. This is the measure of the degree of cyclyzation of the imidazoline feedstock. After spraying, this spectroscopy procedure revealed that the ring content still was around 90%, thus indicating that very little degradation of the product, both in terms of color and ring content, occurred during the prilling operation.

We claim:

1. A stable, free-flowing particulate imidazoline product of the structure

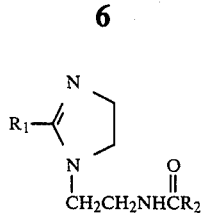

where $R_1$ and $R_2$ independently are a saturated $C_{12}$–$C_{22}$ alkyl group, made by condensing and cyclyzing a fatty acid or ester and a polyamine; wherein the molten, cyclized, solvent-free product is rapidly cooled to a particulate form.

2. The particulate imidazoline product of claim 1 which is rapidly cooled to a particulate form by spraying of said molten, cyclyzed, solvent-free product.

3. The particulate imidazoline product of claim 2 wherein said particulate form is sprayed with a nozzle, spinning disk, or spinning bell.

4. The particulate imidazoline product of claim 1 wherein the molten, cyclized, solvent-free product is rapidly cooled on a chilled roll and attrited to a particulate form.

5. The particulate imidazoline product of claim 1 which has a particle size of about 50–150 microns.

6. A method for making a stable, free-flow particulate imidazoline product of the structure:

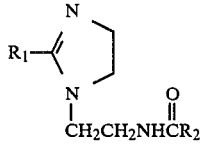

where $R_1$ and $R_2$ independently are a saturated $C_{12}$–$C_{22}$ alkyl group, which comprises condensing and cyclyzing a fatty acid or ester and a polyamine; and
  rapidly cooling the molten, cyclyzed, solvent-free product to a particulate form.

7. The method of claim 6 wherein said moltent product is sprayed to a particulate form.

8. The method of claim 7 wherein said spraying is with a nozzle, a spinning disk, or spinning bell.

9. The method of claim 6 wherein said molten product is rapidly cooled on a chilled roll and attrited to particulate form.

10. The method of claim 6 wherein said particulate form product has a particle size ranging from about 50 to 150 microns.

* * * * *